(12) United States Patent
Slenker et al.

(10) Patent No.: US 9,339,172 B2
(45) Date of Patent: May 17, 2016

(54) METHODS FOR BIOFILM REMOVAL

(75) Inventors: Dale E. Slenker, Jacksonville, FL (US); Cecil "Bo" O. Lewis, Jacksonville, FL (US); Gerould W. Norman, Jacksonville, FL (US); John R. Prisco, Jacksonville, FL (US)

(73) Assignee: Medtronic Xomed, Inc., Jacksonville, FL (US)

( * ) Notice: Subject to any disclaimer, the term of this patent is extended or adjusted under 35 U.S.C. 154(b) by 606 days.

(21) Appl. No.: 12/886,215

(22) Filed: Sep. 20, 2010

(65) Prior Publication Data
US 2011/0009699 A1 Jan. 13, 2011

Related U.S. Application Data

(62) Division of application No. 11/621,453, filed on Jan. 9, 2007, now abandoned.

(51) Int. Cl.
*A61B 1/00* (2006.01)
*A61B 1/12* (2006.01)
*A61M 31/00* (2006.01)
*A61B 1/015* (2006.01)
*A61B 1/005* (2006.01)
(Continued)

(52) U.S. Cl.
CPC .............. *A61B 1/015* (2013.01); *A61B 1/0051* (2013.01); *A61B 1/00091* (2013.01); *A61B 1/00135* (2013.01); *A61M 1/0064* (2013.01); *A61M 3/0283* (2013.01)

(58) Field of Classification Search
USPC ........ 600/121–125, 155–159; 604/22, 48, 23, 604/26, 43–45, 500, 514, 516; 128/898
See application file for complete search history.

(56) References Cited

U.S. PATENT DOCUMENTS

| | | |
|---|---|---|
| 1,487,252 A | 3/1924 | Lore |
| 1,843,169 A | 2/1932 | McKesson |
| 1,987,907 A | 1/1935 | Jenkins |

(Continued)

FOREIGN PATENT DOCUMENTS

| | | |
|---|---|---|
| KR | 0289606 Y1 | 9/2002 |
| KR | 0439992 B1 | 7/2004 |

(Continued)

OTHER PUBLICATIONS

U.S. Appl. No. 11/697,789, filed Apr. 9, 2007.

(Continued)

*Primary Examiner* — Ryan Henderson
(74) *Attorney, Agent, or Firm* — Dicke, Billig & Czaja, PLLC

(57) ABSTRACT

A method of removing bacterial biofilm from a target site of a human patient. A bacterial biofilm removal system is provided that includes an endoscope, an irrigation duct and an aspiration duct. The endoscope includes a working end. The irrigation duct includes an outlet. The aspiration duct includes an inlet. The endoscope working end, the irrigation duct outlet and the aspiration duct inlet are disposed proximate a target site that includes a layer of bacterial biofilm. The target site is imaged with the endoscope working end. The fluid is dispensed through the irrigation duct outlet toward the target site to mechanically remove at least a portion of the layer of bacterial biofilm. The removed bacterial biofilm and the dispensed fluid are collected with the aspiration duct inlet.

21 Claims, 9 Drawing Sheets

(51) Int. Cl.
*A61M 3/02* (2006.01)
*A61M 1/00* (2006.01)

(56) References Cited

U.S. PATENT DOCUMENTS

| | | |
|---|---|---|
| 2,243,299 A | 5/1941 | Travers |
| 2,280,992 A | 4/1942 | Wright et al. |
| 2,812,765 A | 11/1957 | Tofflemire |
| 3,208,145 A | 9/1965 | Turner |
| 3,452,745 A | 7/1969 | Hutchinson et al. |
| 3,470,876 A | 10/1969 | Barchilon |
| 3,749,090 A | 7/1973 | Stewart |
| 3,980,078 A | 9/1976 | Tominaga |
| 4,282,867 A | 8/1981 | Du Toit |
| 4,299,221 A | 11/1981 | Phillips et al. |
| 4,397,640 A | 8/1983 | Haug et al. |
| 4,408,598 A | 10/1983 | Ueda |
| 4,487,600 A | 12/1984 | Brownlie et al. |
| 4,517,962 A * | 5/1985 | Heckele .................. 600/156 |
| 4,519,385 A | 5/1985 | Atkinson et al. |
| 4,526,573 A | 7/1985 | Lester et al. |
| 4,573,979 A | 3/1986 | Blake |
| 4,583,531 A | 4/1986 | Mattchen |
| 4,604,089 A | 8/1986 | Santangelo et al. |
| 4,617,013 A | 10/1986 | Betz |
| 4,680,026 A | 7/1987 | Weightman et al. |
| 4,696,669 A | 9/1987 | Menhusen |
| 4,708,717 A | 11/1987 | Deane et al. |
| 4,776,840 A | 10/1988 | Freitas et al. |
| 4,801,292 A | 1/1989 | Watson |
| 4,881,523 A | 11/1989 | Heckele |
| 4,911,148 A | 3/1990 | Sosnowski et al. |
| 4,941,872 A | 7/1990 | Felix et al. |
| 4,964,849 A | 10/1990 | Robicsek |
| 4,979,497 A | 12/1990 | Matsura et al. |
| 4,991,565 A | 2/1991 | Takahashi et al. |
| 4,998,527 A | 3/1991 | Meyer |
| 5,100,377 A | 3/1992 | Freitas et al. |
| 5,147,292 A | 9/1992 | Kullas et al. |
| 5,170,774 A | 12/1992 | Heckele |
| 5,199,950 A | 4/1993 | Schmitt et al. |
| 5,201,908 A | 4/1993 | Jones |
| 5,203,769 A | 4/1993 | Clement et al. |
| 5,224,929 A | 7/1993 | Remiszewski |
| 5,230,704 A | 7/1993 | Moberg et al. |
| 5,231,989 A | 8/1993 | Middleman et al. |
| 5,286,253 A | 2/1994 | Fucci |
| 5,295,956 A | 3/1994 | Bales et al. |
| 5,312,327 A | 5/1994 | Bales et al. |
| 5,314,406 A | 5/1994 | Arias et al. |
| 5,318,526 A | 6/1994 | Cohen |
| 5,322,503 A | 6/1994 | Desai |
| 5,328,467 A | 7/1994 | Edwards et al. |
| 5,342,299 A | 8/1994 | Snoke et al. |
| 5,354,267 A | 10/1994 | Niermann et al. |
| 5,372,587 A | 12/1994 | Hammerslag et al. |
| 5,378,234 A | 1/1995 | Hammerslag et al. |
| 5,383,852 A | 1/1995 | Stevens-Wright |
| 5,386,817 A | 2/1995 | Jones |
| 5,397,321 A | 3/1995 | Houser et al. |
| 5,429,596 A | 7/1995 | Arias et al. |
| 5,437,636 A | 8/1995 | Snoke et al. |
| 5,443,445 A | 8/1995 | Peters et al. |
| 5,462,527 A | 10/1995 | Stevens-Wright et al. |
| 5,484,402 A | 1/1996 | Saravia et al. |
| 5,496,314 A | 3/1996 | Eggers |
| 5,520,222 A | 5/1996 | Chikama |
| 5,554,112 A | 9/1996 | Walbrink et al. |
| 5,575,752 A | 11/1996 | Yabe et al. |
| 5,575,753 A * | 11/1996 | Yabe et al. .................. 600/123 |
| 5,575,756 A | 11/1996 | Karasawa et al. |
| 5,607,391 A | 3/1997 | Klinger et al. |
| 5,609,573 A | 3/1997 | Sandock |
| 5,709,698 A | 1/1998 | Adams et al. |
| 5,792,098 A | 8/1998 | Felix et al. |
| 5,842,973 A | 12/1998 | Bullard |
| 5,855,549 A | 1/1999 | Newman |
| 5,928,191 A | 7/1999 | Houser et al. |
| 5,944,689 A | 8/1999 | Houser et al. |
| 5,989,183 A | 11/1999 | Reisdorf et al. |
| 5,993,410 A | 11/1999 | Vincent et al. |
| 6,030,360 A | 2/2000 | Biggs |
| 6,053,172 A * | 4/2000 | Hovda et al. .................. 128/898 |
| 6,086,542 A | 7/2000 | Glowa et al. |
| 6,110,103 A | 8/2000 | Donofrio |
| 6,126,633 A | 10/2000 | Kaji et al. |
| 6,174,280 B1 | 1/2001 | Oneda et al. |
| 6,179,776 B1 | 1/2001 | Adams et al. |
| 6,282,442 B1 | 8/2001 | DeStefano et al. |
| 6,293,957 B1 | 9/2001 | Peters et al. |
| 6,364,853 B1 | 4/2002 | French et al. |
| 6,551,302 B1 | 4/2003 | Rosinko et al. |
| 6,599,237 B1 | 7/2003 | Singh |
| 6,623,445 B1 | 9/2003 | Nelson et al. |
| 6,652,488 B1 | 11/2003 | Cover et al. |
| 6,679,834 B2 | 1/2004 | Stahl et al. |
| 6,712,757 B2 | 3/2004 | Becker et al. |
| 6,712,759 B2 | 3/2004 | Muller |
| 6,746,419 B1 | 6/2004 | Arnett et al. |
| 6,770,050 B2 | 8/2004 | Epstein |
| 6,811,544 B2 | 11/2004 | Schaer |
| 6,863,668 B2 | 3/2005 | Gillespie et al. |
| 6,907,879 B2 | 6/2005 | Drinan et al. |
| 6,918,902 B2 | 7/2005 | French et al. |
| 6,939,293 B2 | 9/2005 | Conteas |
| 6,945,956 B2 | 9/2005 | Waldhauser et al. |
| 7,025,759 B2 | 4/2006 | Muller |
| 7,144,383 B2 | 12/2006 | Arnett et al. |
| 2001/0025134 A1 | 9/2001 | Bon et al. |
| 2002/0173699 A1 * | 11/2002 | Becker et al. .................. 600/114 |
| 2003/0158463 A1 | 8/2003 | Julian et al. |
| 2003/0176769 A1 | 9/2003 | Soble et al. |
| 2003/0181934 A1 | 9/2003 | Johnston et al. |
| 2004/0059191 A1 | 3/2004 | Krupa et al. |
| 2004/0267213 A1 | 12/2004 | Knapp |
| 2005/0033265 A1 | 2/2005 | Engel et al. |
| 2005/0075621 A1 | 4/2005 | Rontal |
| 2005/0080396 A1 | 4/2005 | Rontal |
| 2005/0107853 A1 | 5/2005 | Krespi et al. |
| 2005/0182353 A1 | 8/2005 | Schmidberger et al. |
| 2005/0240147 A1 | 10/2005 | Makower et al. |
| 2005/0272975 A1 * | 12/2005 | McWeeney et al. .......... 600/113 |
| 2006/0004286 A1 | 1/2006 | Chang et al. |
| 2006/0004323 A1 | 1/2006 | Chang et al. |
| 2006/0009678 A1 | 1/2006 | Jaffe et al. |
| 2006/0015009 A1 | 1/2006 | Jaffe et al. |
| 2006/0015010 A1 | 1/2006 | Jaffe et al. |
| 2006/0025652 A1 | 2/2006 | Vargas |
| 2006/0041186 A1 | 2/2006 | Vancaillie |
| 2006/0063973 A1 | 3/2006 | Makower et al. |
| 2006/0069343 A1 | 3/2006 | Rontal |
| 2006/0084910 A1 | 4/2006 | Hoffman |
| 2006/0095066 A1 | 5/2006 | Chang et al. |
| 2006/0100481 A1 | 5/2006 | Soble et al. |
| 2006/0106285 A1 | 5/2006 | Boulais et al. |
| 2006/0111615 A1 | 5/2006 | Danitz et al. |
| 2006/0149127 A1 * | 7/2006 | Seddiqui et al. ............. 600/104 |
| 2006/0210605 A1 | 9/2006 | Chang et al. |
| 2006/0224103 A1 * | 10/2006 | Rontal ............................ 604/22 |

FOREIGN PATENT DOCUMENTS

| | | |
|---|---|---|
| WO | 9405200 | 3/1994 |
| WO | 9422358 A1 | 10/1994 |
| WO | 9505112 | 2/1995 |
| WO | 9505112 A1 | 2/1995 |
| WO | 03158463 A1 | 8/2003 |
| WO | 2005049459 A1 | 6/2005 |
| WO | 20060106285 A1 | 5/2006 |
| WO | 2006063973 A1 | 6/2006 |
| WO | 2008085668 A2 | 7/2008 |

OTHER PUBLICATIONS

U.S. Appl. No. 11/680,781, filed Mar. 1, 2007.

(56) References Cited

OTHER PUBLICATIONS

PCT Search Report (mailed Aug. 20, 2008); 11 pgs.
Y. Zhang et al., "Detection of Streptococcus Pneumoniae in Whole Blood by PCR," Journal of Clinical Microbiology, Mar. 1995, pp. 596-601.
J. Christopher Post, MD et al., "Molecular Analysis of Bacterial Pathogens in Otitis Media with Effusion," JAMA, May 24-31, 1995, vol. 273, No. 20; 7 pgs.
E. M. Liederman, MD et al., "Analysis of Adult Otitis Media: Polymerase Chain Reaction Versus Culture for Bacteria and Viruses," Ann Otol Rhinol Laryngol 107:1998; pp. 10-16.
J. J. Aul, MD et al., "Comparative Evaluation and Culture and PCR for the Detection and Determination of Persistence of Bacterial Strains and DNAs in the Chinchilla Laniger Model of Otitis Media," Ann Otol Rhinol Laryngol 107:1998; pp. 508-513.
L. O. Bakaletz et al., "Blinded Multiplex PCR Analyses of Middle Ear and Nasopharyngeal Fluids from Chinchilla Models of Single- and Mixed-Pathogen-Induced Otitis Media," Clinical and Diagnostic Laboratory Immunology, Mar. 1998, pp. 219-224.
J.R. Dingman et al., "Correlation Between Presence of Viable Bacteria and Presence of Endotoxin in Middle-Ear Effusions," Journal of Clinical Microbiology, Nov. 1998, pp. 3417-3419.
J.W. Costerton, "Introduction to Biofilm," International Journal of Antimicrobial Agents 11 (1999); Dec. 2001; pp. 217-221.
J. Christopher Post, MD, PHD, "Direct Evidence of Bacterial Biofilms in Otitis Media," The Laryngoscope, Dec. 2001; pp. 2083-2094.
J.W. Costerson et al, "Battling Iofilms," Scientific American, Jul. 2001; pp. 75-81.
P.S. Mason et al., "Effect of Bacterial Endotoxin and Middle Ear Effusion on Ciliary Activity: Implications for Otitis Media," The Laryngoscope; Apr. 2002; pp. 676-680.
G.D. Ehrlich, PHD et al., "Mucosal Biofilm Formation on Middle-Ear Mucosa in the Chinchilla Model of Otitis Media," JAMA, Apr. 3, 2002, vol. 287, No. 13; pp. 1710-1715.
R.M. Donlan et al., "Biofilms: Survival Mechanisms of Clinically Relevant Microorganisms," Clinical Microbiology Reviews, Apr. 2002, pp. 167-193.
J. Cryer et al., "Evidence of Bactrial Biofilms in Human Chronic Sinusitis," Department of Otorhinolaryngology—Head and Neck Surgery, University of Pennsylvania Medical Center; 2004; pp. 155-158.
G.T. Rodeheaver, PHD, "Wound Cleansing, Wound Irrigation, Wound Disinfection," Chronic Wound Care: A Clinical Source Book for Healthcare Professionals, Third Edition, 2001; pp. 369-383.
J.N. Palmer MD, "Bacterial Biofilms: Do They Play a Role in Chronic Sinusitis?" Department of Otolaryngology—Head and Neck Surgery, Hospital of Pennsylvania, 2005; pp. 1193-1201.
A.Tripathi, MD et al., "Staphylococcal Exotoxins and Nasal Polyposis: Analysis of Systemic and Local Responses," American Journal of Rhinology, Jul.-Aug. 2005, vol. 19, No. 4; pp. 327-333.
J.E. Dohar, MD, MS et al., "Mucosal Biofilm Formation on Middle-Ear Mucosa in a Nonhuman Primate Model of Chronic Suppurative Otitis Media," The Laryngoscope, Aug. 2005; pp. 1469-1472.
B.J. Ferguson MD et al., "Demonstration of Biofilm in Human Bacterial Chronic Rhinosinusitis," American Journal of Rhinology, Sep.-Oct. 2005, vol. 19, No. 5, pp. 452-457.
L. Hall-Stoodley, PHD et al, "Direct Detection of Bacterial Biofilms on the Middle-Ear Mucosa of Children with Chronic Otitis Media," JAMA, Jul. 12, 2006, vol. 296, No. 2, pp. 202-211.
Z. Bendouah, BSC et al., "Biofilm Formation by *Staphylococcus aureus* and Pseudomonas Aeruginosa is Associated with an Unfavorable Evolution After Surgery for Chronic Sinusitis and Nasal Polyposis," American Academy of Otolaryngology—Head and Neck Surgery Foundation; 2006; pp. 991-996.
AU Examiner's First Report on Patent Application No. 2007342189, dated Mar. 30, 2012.
Office Action for U.S. Appl. No. 11/621,453, dated Dec. 29, 2009.

* cited by examiner

METHODS FOR BIOFILM REMOVAL

REFERENCE TO RELATED APPLICATION

This application is a divisional of U.S. application Ser. No. 11/621,453, filed Jan. 9, 2007, which is incorporated herein in its entirety by reference.

BACKGROUND

Bacterial biofilms develop in variety of bodily cavities, including those of the ear, such as the middle ear, and of the nose, such as the frontal or maxillary sinuses, for example. Regardless, the bacteria that generate biofilms often (but not necessarily) are a result of inflammatory insult to tissues, including inflammation arising due to fungi, temperature and pressure changes, allergens, or other sources. The emergence of bacterial growth and associated symptoms is often a cyclical, escalating process with initiation of the inflammatory process facilitating increased bacterial production, which, in turn, causes more inflammation, and so forth. Once bacterial growth has been established, the bacteria will often aggregate, stop dividing, and begin forming protective bacterial biofilm layers, or "slime layers," comprised of polysaccharide matrices.

The protective bacterial biofilm interferes with the body's natural immune response as well as traditional methods of treatment, often times resulting in chronic, recurrent infections and associated symptoms. In particular, the bacteria emit exotoxins, which incite the body's immune system to respond with white cells. However, the bacterial biofilm interferes with the efficacy of the white cells' ability to attack the bacteria. The biofilm can also act as a barrier against topical administration of antibiotics and other medicaments. Biofilm-forming bacteria also present obstacles to traditional, antibiotic treatments that act to kill dividing bacteria. In particular, the bacteria in a biofilm-forming state may have already ceased cell division, rendering such antibiotics largely ineffective.

For example, relative to chronic rhinosinusitis and other similar ailments, bacteria in the nose can be viewed as a continuum. Some bacterias (e.g., certain strains of pseudomonas and staph aureus) form robust biofilms. Others (e.g., h. flu) form relatively mild biofilms. The biofilms may or may not include or contain fungi. Each of these microbes has a somewhat different or complimentary inflammatory pathway and interacts with the host's immune system differently. For example, staph aureus produces a lipopolysaccharide matrix that acts as an antigen and causes a host response, as well as toxins (e.g., staph exotin A and B, toxic shock syndrome toxin 1 and 2) that can produce an antigenic and even hyperantigenic (hyperinflammatory) response. Other microbes can also produce inflammatory-inciting toxins.

Functional endoscopic sinus surgery (FESS) is a minimally invasive surgical procedure used to treat sinusitis, an infection of the sinuses. FESS opens up sinus air cells and sinus ostia (openings) with an endoscope. The use of FESS as a sinus surgical method has now become widely accepted. For reference, the term "functional" is meant to distinguish this type of endoscopic surgery from non-endoscopic, more conventional sinus surgery procedures.

The purpose of FESS is typically to restore normal drainage of the sinuses, which requires ventilation through the ostia. In particular, a muco-ciliary transport process maintains a constant flow of mucus out of the sinuses with the hair-like cilia of a ciliated epithelium layer acting to direct the flow of mucus toward the ostia. Where there is insufficient ventilation or mucous transportation, infection and inflammation can result, a condition known as sinusitis. Sinusitis often develops from an infection where the maxillary and frontal sinuses meet near the nose or, occasionally, from a dental infection. Regardless, sinusitis causes the cilia to work less efficiently and causes the mucous membranes of the sinuses to become engorged, resulting in obstruction of the ostia. The ensuing lack of ventilation and drainage produce conditions which are ripe for bacterial infection, including biofilm-forming bacteria. As described above, such bacterial biofilms often interfere with effective treatment of bacterial infections, such as chronic rhinosinusitis.

With the foregoing background, it has been postulated that effective treatment of recurrent, chronic inflammatory diseases, such as sinusitis, including chronic rhinosinusitis, requires therapies addressing associated bacterial infections and bacterial biofilms.

SUMMARY

Some embodiments address a system for removal of bacterial biofilm from a target site of a human patient. Some systems include an irrigation duct, a nozzle, an aspiration duct, an endoscope, and a removable endoscope sheath. The irrigation duct is in communication with a fluid source. The nozzle communicates with the irrigation duct, the nozzle positioned to dispense the fluid directly at a target site. The aspiration duct is in communication with a vacuum source, the aspiration duct terminating at a distal inlet for aspirating fluid dispensed from the nozzle. The endoscope has an elongated insertion tube defining a working end adapted to facilitate imaging the target site. The removable endoscope sheath provides a barrier over at least a portion of the insertion tube during imaging. In particular, at least one of the irrigation duct and the aspiration duct is associated with the endoscope sheath.

Other embodiments relate to endoscope sheaths for use in removing bacterial biofilm from a target site of a human patient. Some sheaths include an elongated, flexible outer sleeve adapted to receive an insertion tube of an endoscope. The outer sleeve defines a distal end maintaining a viewing window. The sheath also includes an irrigation duct formed as an elongated tube having a distal end maintaining a nozzle. The nozzle is secured adjacent the viewing window and is oriented to direct a pressurized stream of fluid away from the viewing window and directly against a layer of bacterial biofilm to mechanically remove the bacterial biofilm without substantially damaging an underlying structure of the target site.

Still other embodiments relate to methods of removing bacterial biofilm from a target site of a human patient. Some methods include providing a system for removal of bacterial biofilm from a target site. The system includes an endoscope having an insertion tube defining a working end, an irrigation duct connected to a nozzle, an aspiration duct having an inlet, and a removable endoscope sheath for covering the insertion tube. At least one of the irrigation duct and the aspiration duct is part of the removable endoscope sheath. Each of the working end of the endoscope, the inlet of the aspiration duct, and the nozzle, respectively, is disposed proximate the target site, the target site including a layer of bacterial biofilm adhered to a surface. The target site is imaged with the working end of the endoscope. A flow of fluid is dispensed through the nozzle, via the irrigation duct, toward the target site to mechanically remove a substantial portion of the layer of bacterial biofilm from the surface. The removed bacterial biofilm and the dispensed fluid are collected with the inlet end of the aspiration duct. Unlike conventional treatment techniques, the method can interrupt the inflammatory process of a patient by eradicating the underlying biofilm and source of toxins and other antigens and harbor for fungi.

DETAILED DESCRIPTION

Aspects of embodiments described herein relate to systems, methods, and apparatuses for one or more of reducing, removing, or preventing growth of bacterial biofilms. In particular, surgical biofilm removal systems, methods, and apparatuses adapted for such use will be understood with reference to the text and accompanying drawings.

Figure 1:
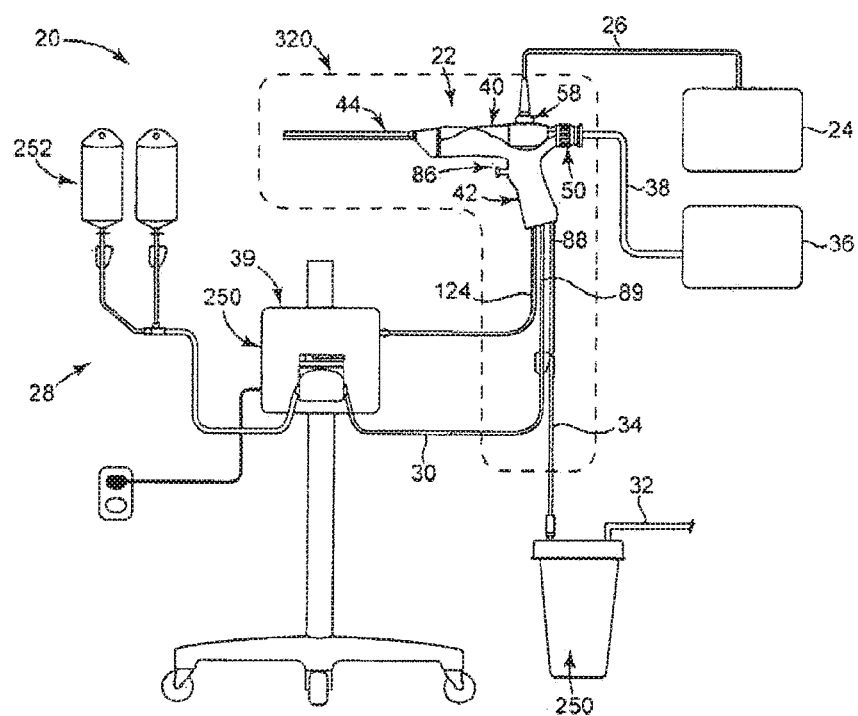
FIG. 1 is a simplified, side view of a system for removal of bacterial biofilm, according to some embodiments.

FIG. 1 shows a surgical biofilm removal system 20, according to some embodiments. The system 20 includes a biofilm removal surgical instrument 22, a light source 24, a light connector 26, a fluid source 28, a fluid connector 30, a vacuum source 32, a vacuum connector 34, an imaging device 36, an imaging connector 38, and a controller 39. In general terms, the light source 24 provides light to the instrument 22 through the light connector 26; the fluid source 28 provides fluid to the instrument 22 through the fluid connector 30; and the vacuum source 32 provides vacuum flow, or aspiratory flow, to the instrument 22 through the vacuum connector 34. The controller 39 controls operation of the system 20 and is shown as being associated generally with the fluid source 28, although the controller 39 is optionally a stand-alone device or physically associated with any of the other system components, including, for example, the instrument 22.

In some embodiments, the instrument 22 includes an endoscope 40, a handle 42, and a removable endoscope sheath 44. In general terms, the endoscope 40 is secured relative to the handle 42, with the handle 42 being used, in part, to facilitate maneuvering of the endoscope 40. The sheath 44 is secured over the endoscope 40, and in some embodiments, the sheath 44 is also secured to the handle 42. The sheath 44 provides a protective barrier for the endoscope 40 and is adapted to facilitate delivery of pressurized fluid in substantially removing a layer of biofilm (not shown), as subsequently described.

Figure 2:
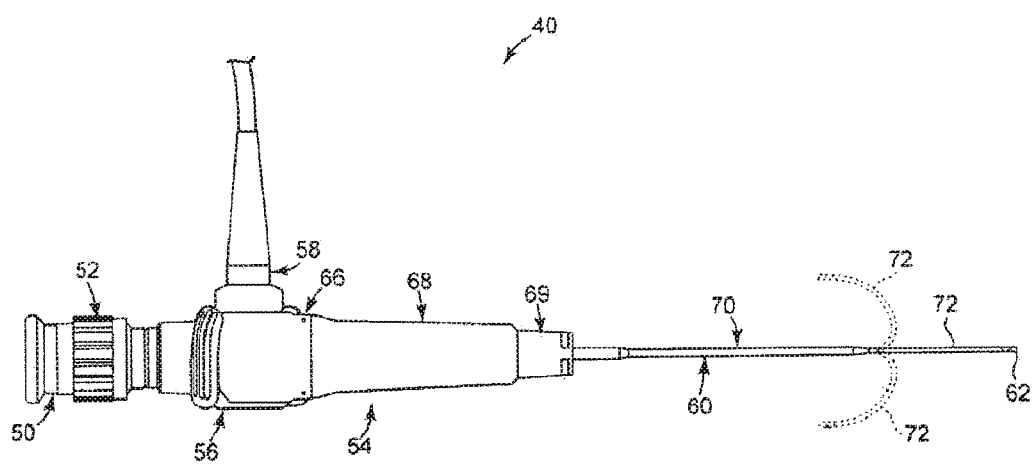
FIG. 2 is a side view of an endoscope useful with the system of FIG. 1.
Figure 10:
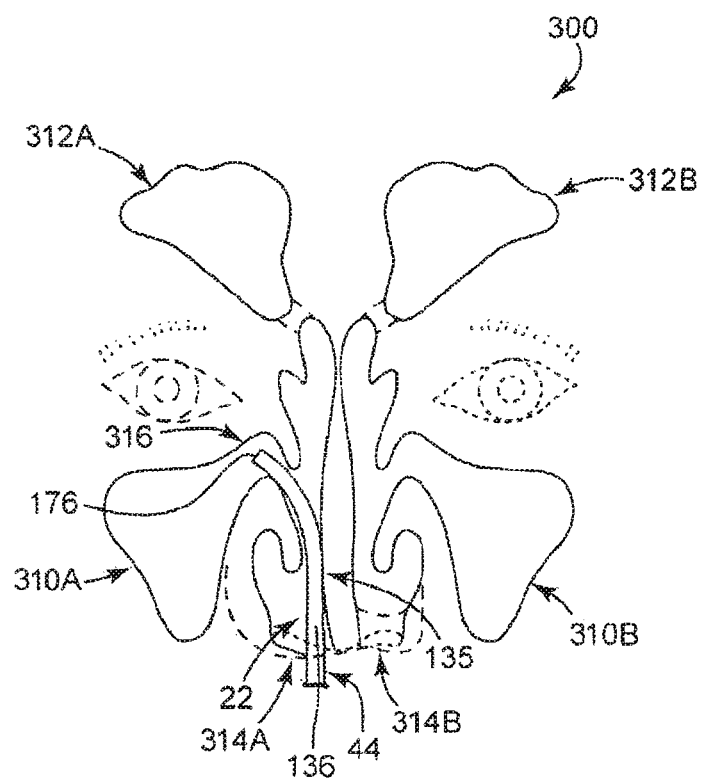
FIG. 10 illustrates use of the instrument of FIG. 9 relative to a human anatomy otherwise shown in simplified form.

As shown in FIG. 2, the endoscope 40 can include various optical components and is generally adapted to image internal bodily structures (FIG. 10). In some embodiments, the endoscope 40 includes an eyepiece 50, a focus ring 52, a housing 54, a control assembly 56, a connection post 58, and an insertion tube 60 that defines a working end 62 of the endoscope 40. In general terms, at least a portion of the insertion tube 60 is disposed inside a human body (not shown) with the working end 62 of the endoscope 40 being disposed at a target site (FIG. 10) to be imaged. "Imaging," "adapted to image," and similar language should be understood to be inclusive of direct visualization through the optical components of the endoscope 40 as well electronic visualization and/or data analysis via electronic imaging, for example using the imaging device 36 (FIG. 1) or other electronics.

In some embodiments, the eyepiece 50 is connected to the housing 54 for direct visualization and/or electronic visualization as referenced above, with the focus ring 52 being disposed about the eyepiece 50 and usable to bring images, or image data, into focus. The housing 54 maintains various optical components of the endoscope 40 and includes a body portion 66 and a neck portion 68. The body portion 66 is relatively bulbous in shape. In turn, the neck portion 68 extends in a tapering manner from the body portion 66 and distally forms an annular connector flange 69 from within which the insertion tube 60 projects.

With continued reference to FIG. 2, in some embodiments, the control assembly 56 and the connection post 58 are maintained by the body portion 66. In turn, the insertion tube 60 is maintained by the neck portion 68 and projects from the connector flange 69 as referenced above. During operation, the control assembly 56 is adapted to control selective bending of the insertion tube 60. The connection post 58 is adapted for connection to the light connector 26, which, in combination with other components of the endoscope 40, provides light at the working end 62 of the endoscope 40.

In some embodiments, the insertion tube 60 includes optical components, such as a fiber-optic bundle (not shown), and is substantially elongate, defining a proximal portion 70, which is connected to the housing 54, and a distal portion 72, which, more specifically, defines the working end 62 of the endoscope 40. The proximal portion 70 is substantially rigid while the distal portion 72 is adapted to be selectively bendable as indicated generally by broken lines in FIG. 2. For example, the distal portion 72 is optionally formed of a flexible material, a series of links, vertebrae, or is otherwise suited to embody bendability. The endoscope 40 includes components for actuating the distal portion 72, including those known to one having ordinary skill in the art, where the control assembly 56 is operable by a user to actuate bending of the distal portion 72 to aim the working end 62 in a desired direction.

For reference, FIG. 2 shows the distal portion 72 in several positions with the use of broken lines. Although, the direction of bending is shown as being within a plane of the drawing sheet, or within a "drawing plane," it should be understood that the distal portion 72 additionally or alternatively is selectively bendable in a plane orthogonal to the drawing plane, or any number of planes for that matter. It should also be noted that, in other embodiments, both the proximal and distal portions 70, 72 are substantially flexible, or alternatively, substantially rigid. In still other embodiments, the proximal portion 70 is selectively bendable and/or substantially flexible, while the distal portion 72 is substantially rigid. From this, it is readily understood that a variety of endoscope configurations are contemplated in association with the instrument 22 (FIG. 1).

During operation of the endoscope 40, light is optionally provided to the working end 62 to illuminate an internal bodily structure or other target site being imaged, with associated images, or image data, being transmitted back from the working end 62 through the insertion tube 60 to the eyepiece 50 and/or associated electronic devices, such as the imaging device 36.

Returning to FIG. 1, the handle 42 can similarly assume a variety of forms. One example configuration of the handle 42 is shown in greater detail in FIGS. 3 and 4, and includes or defines an interior 80 and optionally includes a grip portion 82, a support portion 84, a trigger assembly 86, first tubing 88, and a second tubing 89. As a point of reference, the tubings 88, 89 are removed from the view of FIG. 3 to better illustrate other features of the handle 42.

In some embodiments, the grip portion 82 extends from a butt end 90 and can be characterized as being structured according to a pistol-grip configuration. In terms of use, the grip portion 82 is ergonomically designed to assist a user (not shown) with grasping and manipulating the instrument 22 (FIG. 1) during use. Alternatively, the grip portion 82 can assume a variety of other shapes and/or sizes, and defines at least a portion of the interior 80 along which the trigger assembly 86 and the first and second tubings 88, 89 are maintained, as described below.

Figure 3:
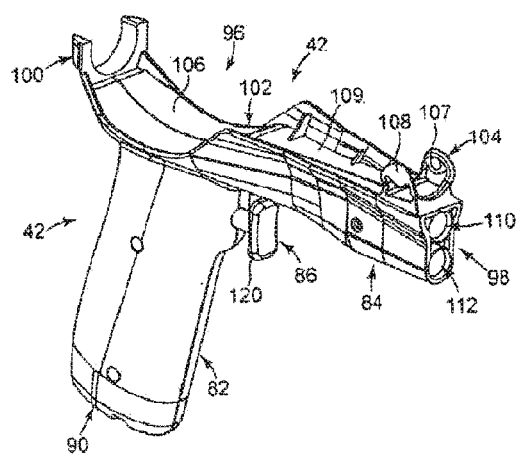
FIG. 3 is a perspective view of a handle portion of the system of FIG. 1.

With specific reference to FIG. 3, the support portion 84 is connected to the grip portion 82, and in some embodiments is integrally formed with the grip portion 82, for example via injection molding. Regardless, the support portion 84 forms a scope cradle 96 adapted to releasably retain the endoscope 40 (FIG. 2), and a sheath interface 98 adapted to releasably retain the sheath 44 (FIG. 1).

The scope cradle 96 includes or defines a proximal bracket 100, a housing carriage 102, and a distal bracket 104. The proximal bracket 100 is substantially U-shaped and is configured to form a complementary fit with the endoscope 40 (FIG. 2), for example a frictional fit with the eyepiece 50 (FIG. 2). The proximal bracket 100 is optionally adapted to flex apart to some extent in order to facilitate a releasable, friction fit with the eyepiece 50. If desired, the proximal bracket 100 additionally or alternatively includes a variety of means for releasably securing the eyepiece 50 in the proximal bracket 100, including, for example, detents, magnets, clips, adhesives, retaining pins, and others.

In turn, the distal bracket 104 is substantially U-shaped according to some embodiments and includes detents 107, 108, where the distal bracket 104 is configured to form a complementary fit with the neck portion 68 of the endoscope 40 (FIG. 2). In this regard, the distal bracket 104 can be adapted to flex apart to some extent in order to facilitate a releasable, friction fit with the neck portion 68. In particular, the detents 107, 108 are used in some embodiments to assist in frictionally and releasably securing the neck portion 68 in the distal bracket 104. If desired, the distal bracket 104 additionally or alternatively includes a variety of means for releasably securing the neck portion 68 in the distal bracket 104, including, for example, additional detents, magnets, clips, adhesives, retaining pins, and others.

The housing carriage 102 is sized and shaped to receive and support the endoscope 40 (FIG. 2) as maintained in the proximal and distal brackets 100, 104. If desired, the housing carriage 102 also includes means for releasably securing the endoscope 40, such as those mentioned in association with the proximal and distal brackets 100, 104. In some embodiments, the housing carriage 102 defines a concave surface 106 adapted to receive the body portion 66 of the endoscope 40 such that there is room for the control assembly 56, and a sloped surface 109 for receiving and/or supporting part of the neck portion 68.

Figure 4:
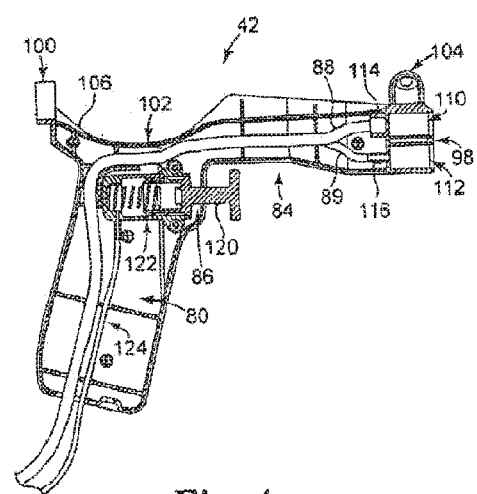
FIG. 4 is a cross-sectional view of the handle of FIG. 3.

With reference between FIGS. 3 and 4, the sheath interface 98 of the grip portion 82 forms a first receptacle 110 and a second receptacle 112 for sealingly receiving complementary features of the sheath 44 (FIG. 1), as will be further elucidated in the ensuing discussion. Additionally, the first and second receptacles 110, 112 optionally form first and second fittings 114, 116 (FIG. 4), respectively, within the interior 80 (FIG. 4) of the handle 42.

In some embodiments, the trigger assembly 86 includes a trigger member 120, a trigger sensor 122, such as a switch, and a connector 124. The trigger member 120 extends external to the grip portion 82 and is adapted to be actuated by a user (not shown), for example via a sliding interface relative to the grip portion 82. As best shown in FIG. 4, the trigger member 120 can be slidably retained within a collet 125 that further retains a biasing device 126 (e.g., a spring) that serves to bias the trigger member 120 to the extended position (relative to the grip portion 82) reflected in FIGS. 3 and 4. Activation of the trigger member 120 thus entails a pushing force being applied thereon, sufficient to overcome a force of the biasing device 126 to thus slide the trigger member 120 inwardly relative to the collet 125. Other actuation arrangements of the trigger member 120 are also acceptable.

The trigger sensor 122 is adapted to provide an output indicative of actuation (e.g., sliding movement) of the trigger member 120, and thus can assume a variety of forms appropriate for sensing movement of the trigger member 120. The connector 124, in turn, is adapted to carry, or transmit, the output from the trigger sensor 122. Thus, the connector 124 can assume a variety of forms (e.g., tubing, wire, etc.), and is connected to the controller 39 (FIG. 1). For example, the connector 124 is connected to the trigger sensor 122 and protrudes externally to the handle 42 through the butt end 90 of the grip portion 82.

With specific reference to FIG. 4, the first tubing 88 of the handle 42 is connected to the first receptacle 110 via the first fitting 114. The first tubing 88 extends through the interior 80 of the handle 42 and out of the butt end 90 of the grip portion 82. The second tubing 89 of the handle 42 is connected to the second receptacle 112 via the second fitting 116. The second tubing 89 also extends through the interior 80 of the handle 42 and out of the butt end 90 of the grip portion 82. As a point of reference, a portion of the second tubing 89 is hidden from view behind the first tubing 88 in FIG. 4.

Figure 5:
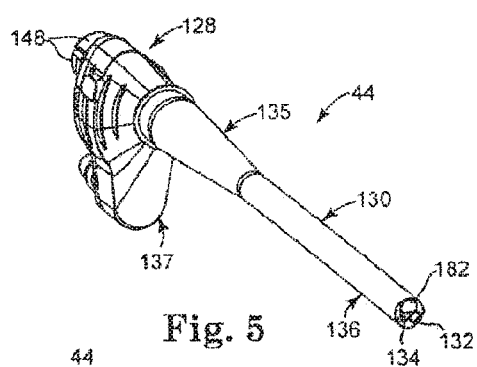
FIG. 5 is a front perspective view of a removable endoscope sheath portion of the system of FIG. 1.

FIG. 5 shows the sheath 44 of the system 20 from a perspective view, according to some embodiments. For reference, the sheath 44, or portions thereof, is optionally disposable. Alternatively, the sheath 44 can be reusable and adapted for sterilization or otherwise adapted to be cleaned. In some embodiments, the sheath 44 includes a manifold 128, a barrier portion 130, an aspiration duct 132 (referenced generally), and an irrigation duct 134 (referenced generally). In general terms, the manifold 128 is adapted to be releasably connected to the endoscope 40 (FIG. 2) and the handle 42 (FIG. 3). In turn, the barrier portion 130 is adapted for insertion into a patient's anatomy.

The barrier portion 130 includes an outer sleeve 135, and, in some embodiments, is assembled to define a distal segment 136. The distal segment 136 is described below as being bendable in association with some embodiments; it will be understood, however, that a remainder of the barrier portion 130 can be substantially flexible, rigid, malleable, or combinations thereof as desired. Alternatively, the distal segment 136 can be substantially rigid and not bendable.

Figure 6:
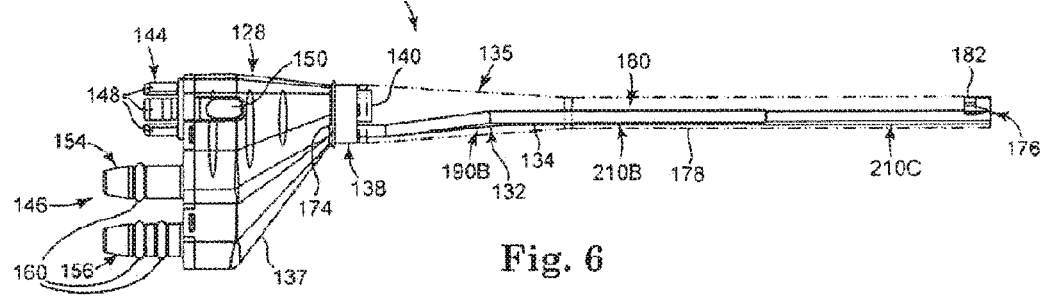
FIG. 6 is a side view of the sheath of FIG. 5, with a portion shown in broken lines.

With additional reference to FIG. 6 (that otherwise illustrates portions of the outer sleeve 135 with broken lines), in some embodiments, the manifold 128 includes or forms a primary frame 137, a sleeve hub 138 and an insertion tube guide 140. The manifold 128 also defines an interior 142 (FIG. 9) and forms a scope connector 144 and a handle interface 146. The scope connector 144 is adapted to be releasably secured to the connector flange 69 (FIG. 2) of the endoscope 40 (FIG. 2).

In some embodiments, the sleeve hub 138 projects distally from the frame 137 and is adapted to form a complementary fit with the barrier portion 130. The insertion tube guide 140 is an annular, hollow body, projecting distally from the sleeve hub 138. The insertion tube guide 140 is adapted to slidably receive the insertion tube 60 (FIG. 2) of the endoscope 40 (FIG. 2) according to some embodiments.

The scope connector 144 extends from the frame 137 opposite the sleeve hub 138, and includes a plurality of projections or fingers 148. In addition, the scope connector 144 can include a first release member 150 and a substantially similar second release member (hidden in the view of FIG. 6) opposite the first release member 150, in some embodiments. In particular, one or more of the plurality of projections 148 are adapted to be deflected upon insertion within the connector flange 69 (FIG. 2) of the endoscope 40 (FIG. 2) to releasably mate therewith. The first release member 150 and the second release member are associated with one or more of the plurality of projections 148 such that depression of the respective release member(s) 150 causes one or more of the plurality of projections 148 to deflect inwardly to release the scope connector 144 from the connector flange 69. In this manner, the scope connector 144 acts according to what can be described as a "spring clip and release" or a "quick connect and release" mechanism in combination with the handle interface 146.

In some embodiments, the handle interface 146 forms a first coupling head 154 and second coupling head 156, which are adapted to be insertable within, as well as form complementary fits with, the first and second receptacles 110, 112 (FIG. 4), respectively, of the handle 42 (FIG. 4). Each of the first and second coupling heads 154, 156 optionally includes a plurality of other sealing means 160, such as o-rings, for forming a vacuum-tight and/or a liquid-tight seal, for example, with the first and second receptacles 110, 112, respectively.

In some embodiments, the outer sleeve 135 includes a substantially cylindrical sleeve body 178 defining a proximal end 174, a distal end 176, and a central lumen or similar open space 180. The outer sleeve 135 also includes a viewing window 182. For reference the distal end 176 is sealed to the viewing window 182, as well as the aspiration and irrigation ducts 132, 134 such that the central lumen 180 is closed off, or sealed, from environment at the distal end 176. However, it is contemplated that in other embodiments, the distal end 176 is not sealed or is open, providing a path into the central lumen 180. As referenced above, in FIGS. 6-8, a border of the sleeve body 178 is shown with broken lines to better allow understanding of features residing within the sleeve body 178.

The sleeve body 178 is optionally formed of a substantially flexible, and, in some embodiments, elastomeric material. Although the figures reflect the sleeve body 178 as being substantially circular in transverse cross-section, it should be understood that, in some embodiments, the sleeve body 178 optionally conforms to the aspiration duct 132 and/or irrigation duct 134 to a greater extent than shown. Additionally or alternatively, the sleeve body 178 is substantially rigid or substantially malleable in other embodiments.

In order to give a point of reference as to the variety of sheath configurations contemplated, it should be noted that in some embodiments, substantially all the sleeve body 178 of the outer sleeve 135 is flexible, or bendable; in other embodiments, the sleeve body 178 is flexible proximate the distal end 176 and more rigid proximate the proximal end 174, or vice versa; and in still other embodiments, substantially all of the sleeve body 178 is substantially rigid.

Figure 7:
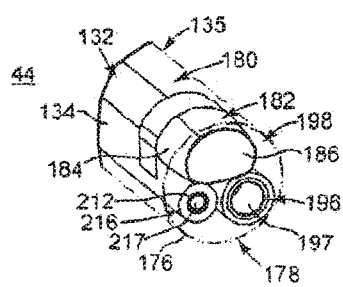
FIG. 7 enlarged, perspective view of a portion of the sheath of FIG. 5 with a portion of the sheath shown in broken lines.

As best shown in FIG. 7, the viewing window 182 includes a housing 184 and a lens 186 secured to the housing 184, where the housing 184 is hollow and adapted to receive the working end 62 (FIG. 2) of the endoscope 40 (FIG. 2) such that the working end 62 abuts or comes in close proximity to the lens 186 upon final assembly. The viewing window 182 is secured within the central lumen 180 at or adjacent the distal end 176 of the sleeve body 178. For example, the viewing window 182 is optionally adhesively secured at the distal end 176. For reference, and as alluded to above, the distal end 176 of the sleeve body 178 is optionally sealed to the lens 186 to help prevent environment at the distal end 176 from entering the central lumen 180.

Figure 8:
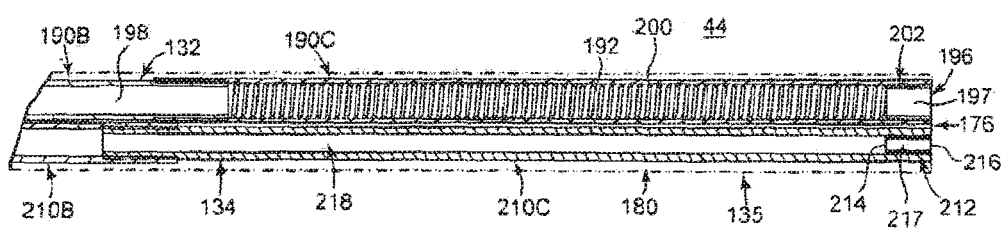
FIG. 8 is an enlarged, top cross-sectional view of a distal portion of the sheath of FIG. 5, with a portion of the sheath shown in broken lines to assist in understanding.
Figure 9:
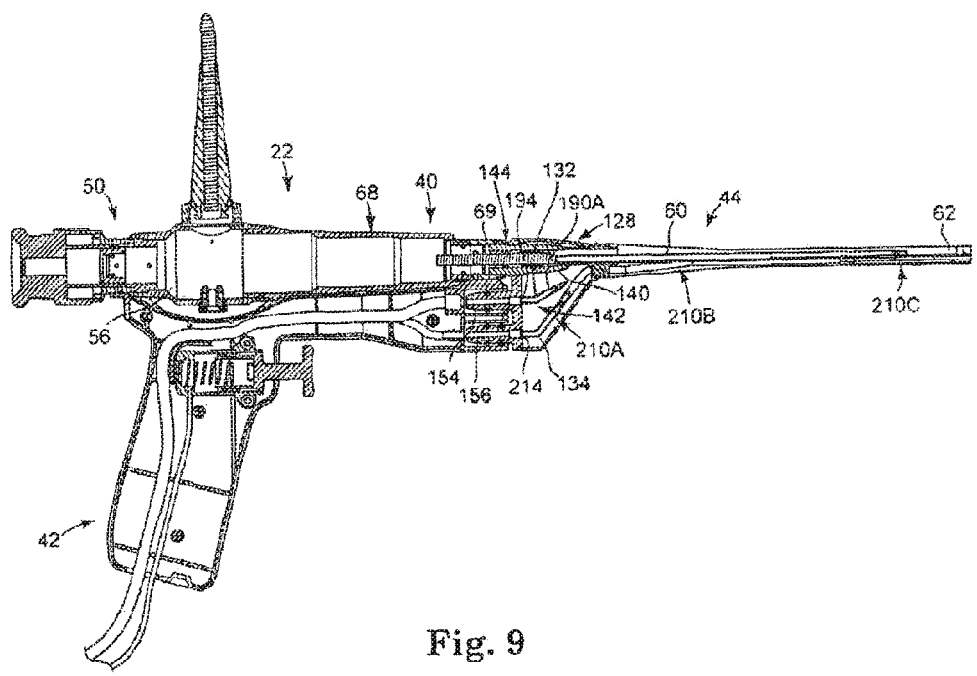
FIG. 9 is a side, cross-sectional view of a surgical instrument portion of the system of FIG. 1, upon final assembly.

With reference to FIGS. 6, 8, and 9, the aspiration duct 132 is formed of, or defined by, a plurality of sections 190, including a manifold section 190A, a proximal sleeve section 190B (largely obscured by the irrigation duct 134 in FIG. 6), and a distal sleeve section 190C. The aspiration duct 132 can be supported by a reinforcement assembly 192 (FIG. 8), and defines a proximal end 194 (FIG. 9), a distal inlet end 196 (FIG. 8), a distal inlet 197 (FIG. 8), and a lumen 198 (FIG. 8) for conveying an aspiratory flow between the proximal and distal ends 194, 196. For reference, the plurality of tubular sections 190 is formed as a single, continuous component; as separate, connected components; or combinations thereof, according to various embodiments. The aspiration duct 132, is optionally substantially flexible, substantially rigid, substantially malleable, or combinations thereof.

As best shown in FIG. 9 (that otherwise illustrates the instrument 22 upon final assembly), the manifold section 190A is optionally substantially rigid and/or formed as a part of the manifold 128, for example being injection molded as a single piece with the manifold 128. In other embodiments, the manifold section 190A is formed of a separate, substantially elongate, flexible, tube (or "cannula"). Regardless, the manifold section 190A of the aspiration duct 132 is in fluid communication with the first coupling head 154 of the manifold 128 and defines a portion of the lumen 198 (FIG. 8) of the aspiration duct 132.

With specific reference to FIGS. 6 and 8, in some embodiments, the proximal sleeve section 190B (largely hidden) of the aspiration duct 132 is substantially rigid and/or is formed continuously with the manifold section 190A (FIG. 9), for example being injection molded as a single piece with the manifold section 190A. In other embodiments, the proximal sleeve section 190B is formed of a separate, substantially elongate, flexible, tube (or "cannula"), in fluid communication with the manifold section 190A. Regardless, the proximal sleeve section 190B extends distally from, and is in fluid communication with, the manifold section 190A and defines a portion of the lumen 198.

As best shown in FIG. 8, in some embodiments, the distal sleeve section 190C is substantially flexible and/or is formed as a separate, substantially elongate, tube (or "cannula"), in fluid communication with the proximal sleeve section 190B. As will be described in greater detail below, flexibility of the distal sleeve section 190C allows selective bending of the distal portion 72 (FIG. 2) of the endoscope 40 (FIG. 2) according to some embodiments. In other embodiments, the distal sleeve section 190C is substantially rigid and/or is formed continuously with the proximal sleeve section 190B as a single piece. Regardless, the distal sleeve section 196C of the aspiration duct 132 extends distally from, and is in fluid communication with, the proximal sleeve section 190B and defines a portion of the lumen 198.

As mentioned above, the aspiration duct 132, and in particular the distal sleeve section 196C thereof, can be supported by the reinforcement assembly 192. With this in mind, the reinforcement assembly 192 can include a reinforcement member 200 and an end piece 202. The reinforcement assembly 192 is maintained within the distal sleeve section 190C, proximal the distal inlet end 196.

The reinforcement member 200 is optionally a spring-like member which is bendable, yet resistant to being radially collapsed. Thus, the reinforcement member 200 provides the distal sleeve section 190C with some resistance to collapsing, while still being bendable, for example, where the distal sleeve section 190C is otherwise formed of a substantially flexible member that might collapse under the negative pressure of an aspiratory flow. It should also be noted that in other embodiments, the reinforcement member 200 is disposed around the distal sleeve section 190C, or even as an integral component of the distal sleeve section 190C.

The end piece 202 is tubular and is optionally substantially rigid, assisting with reinforcement of the distal sleeve section 190C according to some embodiments. For reference, the end piece 202 and/or the distal inlet end 196 of the aspiration duct 132 is optionally sealed to the distal end 176 of the outer sleeve 135 to help prevent contamination of the central lumen 180 of the outer sleeve 135.

The irrigation duct 134 is similar to the aspiration duct 132, and includes (with combined reference to FIGS. 6, 8, and 9) a plurality of sections 210, including a manifold section 210A, a proximal sleeve section 210B, and a distal sleeve section 210C. The irrigation duct 134 is fluidly connected to a nozzle 212, and defines a proximal end 214 (FIG. 9), a distal outlet end 216, a distal outlet 217 (FIG. 7), and central lumen 218 for conveying a fluid (not shown) between the proximal and distal ends 214, 216 and out the distal outlet 217. For reference, the plurality of sections 210 is formed as a single, continuous component; as separate, connected components; or combinations thereof, according to various embodiments. The irrigation duct 134, is optionally substantially flexible, substantially rigid, substantially malleable, or combinations thereof. Although, it should be noted that the distal sleeve section 210C is bendable in some embodiments to accommodate flexibility of the bendable section 136 (FIG. 5) of the barrier portion 130 (FIG. 5).

With reference to FIG. 9, the manifold section 210A is optionally substantially rigid and/or formed as a part of the manifold 128, for example being injection molded as a single piece with the manifold 128. In other embodiments, the manifold section 210A is formed of a separate, substantially elongate, flexible, hollow, tube, which can also be described as a "cannula." Regardless, the manifold section 210A of the irrigation duct 134 is in fluid communication with the second coupling head 156 of the manifold 128 and defines a portion of the lumen 218 (FIG. 8) of the irrigation duct 134.

With reference between FIGS. 6 and 9, in some embodiments, the proximal sleeve section 210B is substantially rigid and/or is formed continuously with the manifold section 210A, for example being injection molded as a single piece with the manifold section 210A. In other embodiments, the proximal sleeve section 210B is formed of a separate, substantially elongate, flexible, tube (or "cannula"), in fluid communication with the manifold section 210A. Regardless, the proximal sleeve section 210B of the irrigation duct 134 extends distally from, and is in fluid communication with, the manifold section 210A and defines a portion of the lumen 218 (FIG. 8) of the irrigation duct 134.

In some embodiments, the distal sleeve section 210C is substantially flexible and/or is formed as a separate, substantially elongate, tube (or "cannula"), in fluid communication with the proximal sleeve section 210B. As will be described in greater detail below, flexibility of the distal sleeve section 210C allows selective bending of the bendable section 136 of the endoscope 40 according to some embodiments. In other embodiments, the distal sleeve section 210C is substantially rigid and/or is formed continuously with the proximal sleeve section 210B as a single piece. Regardless, the distal sleeve section 210C of the irrigation duct 134 extends distally from, and is in fluid communication with, the proximal sleeve section 210B and defines a portion of the lumen 218 (FIG. 8) of the irrigation duct 134.

With reference to FIG. 8, the nozzle 212 is a hollow, tube (or "cannula") adapted to act as a flow restricter in some embodiments. The nozzle 212 defines the distal outlet 217 in some embodiments, causing fluid to be ejected from the irrigation duct 134 according to a desired flow rate and/or flow pattern, such as, a jet, spray, stream, aerosol, or other flow pattern. The nozzle 212 is maintained within the central lumen 218 at the distal sleeve section 210C, at or adjacent the distal outlet end 216 of the irrigation duct 134. In some embodiments, the nozzle 212 and/or the distal outlet end 216 of the irrigation duct 134 is sealed to the distal end 176 of the outer sleeve 135 to help prevent environmental contamination of the central lumen 180 of the outer sleeve 135 while still allowing a flow of fluid through the nozzle 212 and out of the distal outlet 217.

With reference to FIG. 6, the sheath 44 is assembled according to some embodiments by disposing the proximal and distal sleeve sections 190B, 190C, 210B, 210C, of the aspiration duct 132 and the irrigation duct 134, respectively, within the central lumen 180 of the outer sleeve 135. In turn, the proximal end 174 of the outer sleeve 135 is secured, releasably or otherwise, over the sleeve hub 138 of the manifold 128. The distal ends 196, 216 of the aspiration and irrigation ducts 132, 134, respectively, are sealed to the distal end 176 of the outer sleeve 135 in some embodiments to help close the lumen 180 of the outer sleeve 135 from environment at the distal end 176 thereof. However, it should be understood that the aspiration and irrigation ducts 132, 134 themselves, and in particular the central lumens 198, 218 (FIG. 8), respectively, at the distal inlet end 196 and distal outlet end 216 are exposed, or open, through the distal end 176 of the outer sleeve 135 such that irrigant can pass out of the irrigation duct 134 and inspiratory flow and associated, aspirated matter can pass into the aspiration duct 132 proximate the distal end 176 of the outer sleeve 135.

With reference to FIG. 7, in some embodiments, the distal outlet end 216 of the irrigation duct 134 is secured relative to the distal end 176 of the outer sleeve 135 such that the nozzle 212 (referenced generally) points longitudinally in substantially the same direction as the viewing window 182. In this manner, the working end 62 (FIG. 2) endoscope 40 (FIG. 2) can be used to observe an area or target that a flow of irrigant from the nozzle 212 is striking when the irrigant is within a field of view of the endoscope 40. In other embodiments, the nozzle 212 and the viewing window 182 are oriented to define an intersection point (i.e., where the longitudinal line-of-sight from the viewing window 182 intersects the longitudinal line of flow from the nozzle 212) distal to the viewing window 182, to promote viewing of the flow of irrigant proximate the intersection point. The distal inlet end 196 of the aspiration duct 132 is also secured relative to the outer sleeve 135 and/or irrigation duct 134, according to some embodiments, such that the distal inlet end 196 points in a substantially similar direction as the nozzle 212 and/or viewing window 182, although other orientations are also contemplated.

In view of the above, it should be understood that in some embodiments, at least one of the aspiration and irrigation ducts 132, 134 is associated with the sheath 44. As used herein, "associated with the sheath" is indicative of at least one of the ducts 132, 134, respectively, being included as a part of the sheath 44, such as being disposed or formed within the outer sleeve 135, on the outer sleeve 135, or being secured relative to the outer sleeve 135. Furthermore, it should be understood that in some embodiments, the distal sleeve sections 190C, 210C of the aspiration and irrigation ducts 132, 134, as well as at least a corresponding portion of the outer sleeve 135, respectively, form the bendable section 136 of the barrier portion 130 such that it is repeatably bendable in conjunction with selective bending of the endoscope 40, as previously alluded to, and as subsequently described.

Assembly of the surgical instrument 22 according to some embodiments is described below with reference to FIG. 9. The endoscope 40 is secured to the handle 42 by releasably receiving the eyepiece 50 of the endoscope 40 in the proximal bracket 100 (FIG. 4) of the handle 42. The neck portion 68, and in particular, the connector flange 69, of the endoscope 40, in turn, is releasably received in the distal bracket 104 (FIG. 4) of the handle 42. With the endoscope 40 so-received, the body portion 66 rests over the concave surface 106, while allowing room for actuation of the control assembly 56, with the neck portion 68, in turn, resting over and/or against the sloped area 109 of the housing carriage 102.

In some embodiments, the endoscope 40 is assembled to the sheath 44 as follows. The insertion tube 60 of the endoscope 40 is slid through the scope connector 144 and the insertion tube guide 140 of the manifold 128, and into the central lumen 180 of the outer sleeve 135, such that the working end 62 (referenced generally) is received against the lens 186 (FIG. 7). With the working end 62 so-received, the working end 62 is secured relative to the sheath 44, and in particular relative to the irrigation duct 134, the aspiration duct 132, and the nozzle 212 (FIG. 8).

The endoscope 40 is releasably secured to the handle 42 by inserting the scope connector 144 of the handle 42 into the connector flange 69 of the endoscope 40 to releasably secure the two, as previously referenced. From the foregoing, it should be understood that features and methods for assembling the instrument 22 as provided above are not only releasable, but also quick and intuitive in nature according to some embodiments.

Returning to FIG. 1, other components of the system 20 can assume a variety of forms. For example, the light source 24 can be adapted to provide illumination to the endoscope 40, is secured to the connection post 58 of the endoscope 40 via the light connector 26, and can be of a type known to those of skill in the art. As previously referenced, the light source 24 provides light to the instrument 22, for illuminating a target site (FIG. 10).

The fluid source 28 includes a pump 250 connected to a reservoir 252. In some embodiments, the pump 250 is a peristaltic pump, such as those typically used in association with surgical and/or endoscopic procedures, the pump 250 serving to pressurize a flow of fluid from the reservoir 252 to the instrument 22 as described below. The reservoir 252 includes one or more IV bags, for example, filled with an irrigant, including the irrigating fluids described in U.S. patent application Ser. No. 11/431,495, entitled, "Biofilm Extracellular Polysaccharide Solvating (EPS) System," and filed on May 10, 2006, the contents of which are incorporated herein by reference. In some embodiments, the irrigant includes medicaments, including those adapted to interfere with bacterial biofilm re-growth, surfactants, gels, antimicrobials, steroids, growth hormones, chemicals for reducing biofilm adhesion force, and others.

The fluid source 28 is fluidly connected to the instrument 22 via the fluid connector 30, which is a tubing set, for example. In particular, the fluid connector 30 is in fluid communication with (or is formed as part of) the second tubing 89 of the handle 42. The second tubing 89, in turn, is in fluid communication with the irrigation duct 134 (FIG. 9) of the sheath 44 upon assembly of the instrument 22. This places the irrigation duct 134 in fluid communication with the fluid source 28. It should also be noted that, in some embodiments, the fluid connector 30 can include an auxiliary inlet or port (not shown), for introducing medicaments into irrigant (not shown) flowing from the fluid source 28 and to irrigation duct 134, for example, medicaments such as those previously referenced.

The vacuum source 32 (referenced generally) is adapted to provide an aspiratory, or vacuum flow, to the instrument 22 via the vacuum connector 34. The vacuum source 32 is optionally of a type commonly used in association with surgical and/or endoscopic procedures and can include a collection canister 250 fluidly connecting a source of negative pressure (not shown) to the vacuum connector 34. The vacuum connector 34 is placed into fluid communication with, or is formed as part of, the first tubing 88 of the handle 42 and the source of negative pressure 32. The first tubing 88, in turn, is in fluid communication with the aspiration duct 132 (FIG. 9) of the sheath 44 upon assembly of the instrument 22. In this manner, the aspiration duct 132 is in fluid communication with the vacuum source 32 according to some embodiments, such that an aspiratory flow is "pulled" through the aspiration duct 132 with the vacuum source 32. Additionally, in some embodiments, the canister 250 serves as a disposal means, such as a disposal tank, for collecting debris and other matter aspirated using the instrument 22, including those generally used in surgical and/or endoscopic procedures.

The imaging device 36 is optionally an image sensor, such as a video camera, display, and/or other imaging electronics, including those typically used in association with endoscopic procedures. The imaging device 36 is connected to the instrument 22 via the imaging connector 38. In particular, the imaging connector 38 is placed into optical communication with the eyepiece 50 of the endoscope 40. As is conventionally known, the imaging device 36 and the endoscope 40 are used for imaging before, during, and/or after a surgical procedure using the instrument 22.

As previously referenced, the controller 39 controls operation of the system 20 and is designated as being physically associated with the fluid source 28, although the controller 39 is optionally a stand-alone device or physically associated with any of the other system components, including, for example, the handle 42 or sheath 44 of the instrument 22. In some embodiments the controller 39 includes a microchip, memory, and/or other appropriate control electronics.

The controller 39 is placed in communication with the instrument 22 and the fluid source 28. For example, the controller 39 is electrically connected to the instrument 22 via the connector 124 of the trigger assembly 86 (referenced generally). The controller 39 can also be placed in direct or indirect communication with the fluid source 28 and/or vacuum source 32 via wiring or alternate means as appropriate, for example using wireless transmitters and receivers. Regardless, in some embodiments, actuation of the trigger assembly 86 sends a signal to the controller 39, which in turn activates the fluid source 28 to provide a flow of irrigant to the instrument 22 as desired. In some embodiments, the controller 39 can further control operation of the vacuum source 32, either directly or indirectly. It should also be noted that the controller 39 can be programmed to operate the system 20 according to a variety of desired irrigation and/or aspiration profiles, including ramped actuation, time delays, varied flow patterns, and others.

The surgical biofilm removal system 20 can be employed to perform a variety of procedures at various anatomical locations of a patient. By way of but one example, FIG. 10 illustrates internal bodily structures 300 of a patient, including sinus cavities such as maxillary sinuses 310A, 310B and frontal sinuses 312A, 312B, which are accessed through nares 314A, 314B. It should be noted that external features of the patient, including the nares 314A, 314B, are shown in dotted lines. For some procedures with which the system 20 is useful (e.g., a patient suffering from chronic rhinosinusitis), a first target site 316 can be designated in association with a surface of the maxillary sinus 310A for description of a surgical methodology for substantially removing a layer of biofilm. It should be understood, however, that similar principles apply across embodiments, including a variety of target sites associated with a variety of internal bodily structures, such as sinus cavities (the maxillary, frontal, sphenoid, and others), cavities of the ear (the middle ear, and others), etc. With that in mind, in some embodiments, the first target site 316 is ciliated epithelium of the maxillary sinus 310A that has an associated layer of bacteria and associated biofilm (not shown). In other embodiments, the target site 316 is an artificial structure (not shown), such as sinus packing or a stent covered with a layer of bacterial biofilm, for example.

With combined reference to FIG. 1 and FIG. 10, and with the foregoing description of the system 20 in mind, some methods of removing bacterial biofilm (not shown) from one or more target sites internal to a patient include the following: setting up the system 20; inserting a distal portion of the instrument 22 into the maxillary sinus 310A; aiming the distal portion of the instrument 22 (in particular the nozzle 212 (FIG. 8)) at the target site 316; delivering a pressurized flow of irrigant (not shown) from the irrigation duct 134 (FIG. 8) and the nozzle 212 to the target site 316 to remove a substantial amount of the bacterial biofilm; and aspirating the irrigant, removed biofilm, and/or bodily secretions (not shown) away from the target site 316 through the distal inlet 197 (FIG. 7) of the aspiration duct 132 (FIG. 8).

In some embodiments, a functional endoscopic sinus surgery (FESS) is also performed prior to, or concurrently with, insertion of the instrument 22. For example, the endoscope 40, and more generally, the instrument 22, is optionally adapted for, and/or used in combination with other implements as desired for, gaining access to the target site 316 as part of an FESS procedure.

Setting up the system 20 according to some embodiments includes releasably securing the endoscope 40, the handle 42, and the sheath 44 together as previously described, where friction fit, detent, and/or "spring clip and release" mechanisms according to some embodiments provide a releasable assembly, that is quick and intuitive in nature. Other system components, including the light source 24, fluid source 28, vacuum source 32, imaging device 36, and controller 39 are connected to the instrument 22 as appropriate. Additionally, a sterile barrier 320 (illustrated schematically in FIG. 1), such as sheeting or others commonly used in surgical and/or endoscopic procedures, is set up around the instrument 22 and the patient in some embodiments to help maintain a sterile operating environment.

As referenced above, although some embodiments of acting upon a target site to remove a layer of biofilm are described with reference to the maxillary sinus 310A and the target site 316, it should be understood that biofilm removal at with other target sites and/or other cavities, including sinus cavities or cavities of the middle ear (not shown), proceeds in a substantially similar manner. With this in mind, inserting the distal portion of the instrument 22 into the maxillary sinus 310A includes a practitioner (not shown) grasping the handle 42 and inserting the working end 62 (FIG. 2) of the endoscope 40 (FIG. 2) (as positioned within the sheath 44 as previously described) into the nares 314A and toward the maxillary sinus 310A. In some embodiments, the endoscope 40 acquires images during insertion in order to assist a surgeon or other practitioner guiding the instrument 22.

With additional reference to FIG. 2, the distal portion 72 of the endoscope insertion tube 60 is then selectively bent using the control assembly 56 to aim the working end 62 of the endoscope 40 in a desired direction and/or to facilitate insertion of the instrument 22 into the maxillary sinus 310A. The distal, bendable section 136 of the sheath 44 is also bent in conjunction with the selective bending of the distal portion 72. In particular, the distal end 176 of the outer sleeve 135, including the viewing window 182 (FIG. 5), is moved with movement of the working end 62 of the endoscope 40. Additionally, the distal ends 196, 216 (FIG. 8) of the aspiration and irrigation ducts 132, 134 (FIG. 8) respectively, as well as the nozzle 212 (FIG. 8) are also aimed, or otherwise track along with the working end 62 of the endoscope 40.

In some embodiments, the user (not shown) determines that the instrument 22 is properly "aimed" or otherwise disposed as desired in the maxillary sinus 310A relative to a target site for debriding. For example, the user optionally determines proper positioning using images acquired with the endoscope 40 and displayed to the user with the imaging device 36. In some embodiments, the user identifies target site 316 by observing the presence/location of the layer of biofilm, for example by evaluating images displayed to the user with the imaging device 36.

The user (not shown) then prompts delivery of a pressurized flow of irrigant to the target site 316 to effectuate removal or eradication of a substantial amount of the bacterial biofilm (not shown) from the target site 316 by squeezing the trigger member 120 (FIG. 3). In response to this actuation, a signal is sent to the controller 39 that in turn prompts activation of the fluid source 28 to provide a flow of irrigant through the irrigation duct 134 (FIG. 8) and the nozzle 212 (FIG. 8). It is contemplated that the flow of irrigant will be directed through the nozzle 212 at a variety of flow rates according to various embodiments, including a flow rate from about 2 ml/s to about 12 ml/s. In some embodiments, the system 20 is adapted to cause pulsed flow through the nozzle 212, in others substantially continuous flow, and in still others, a flow pattern other than pulsed or substantially continuous flow.

In some embodiments, the flow of irrigant dispensed from the nozzle 212 directly impinges upon, or otherwise directly strikes, the target site 316 to mechanically agitate and remove a substantial portion, or substantially all, of the biofilm (not shown). In other words, the nozzle 212 is able to be pointed directly at the target site 316 as previously described when sufficiently accessible with the instrument 22, such that a mechanical "scrubbing" action is accomplished. It should be noted that the pressure and/or flow rate of the irrigant is selected to promote mechanical removal of the biofilm without substantial damage to underlying tissue, such as a ciliated epithelium layer. For example, in some embodiments, a pressure of less than about 50 psi at the target site 316 is selected, although other pressures are contemplated.

In some embodiments, aspiration of bacterial biofilm, bacteria, mucous, secretions, dead tissue, or other unwanted matter is accomplished using the aspiration duct 132 (FIG. 8), for example during and/or after dispensing the irrigant (not shown) against the target site 316. The instrument 22 is operated to selectively or continuously activate the vacuum source 32 in response to the user pulling the trigger member 120 (FIG. 3), for example concurrently with irrigation or with some time differential (for example, before or after irrigation). The unwanted matter is removed from proximate the target site 316 and is optionally directed to the biological collection canister 250 associated with the vacuum source 32.

The systems and methods described above are highly useful in surgically treating various maladies associated with multiple different anatomical locations or target sites. For example, in addition to sinus and inner ear target sites, the systems and methods of the present disclosure can be used to treat target site(s) in patient's lungs (e.g., cystic fibrosis in the respiratory epithelium of the lungs), urological and/or gynecological (e.g., urinary tract infections), etc.

In view of the above, a method for removing biofilm from a surface within an internal bodily cavity (or other target site) under endoscopic visualization is provided according to some embodiments. It should be noted that various functions of the instrument 22 are optionally provided according to alternative embodiments, such as those described below in association with FIGS. 11-14.

Figure 11:
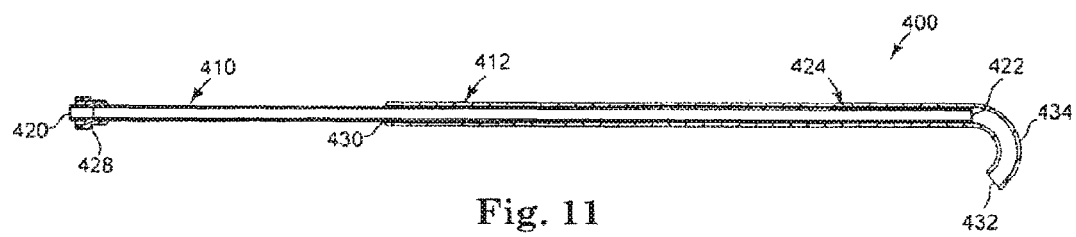
FIG. 11 is a side, cross-sectional view of a duct assembly useful with the system of FIG. 1 in some other embodiments.

FIG. 11 shows a duct assembly 400 optionally forming a part of the system 20 (FIG. 1) according to some other embodiments. In some embodiments, the duct assembly 400 is not otherwise associated with the sheath 44 (FIG. 5) and is usable as a separate, distinct component. With this in mind, the duct assembly 400 includes an inner tube (or "inner cannula") 410 and an outer tube (or "outer cannula") 412.

The inner tube 410 is elongate and hollow, and defines a proximal end 420, a distal end 422, and a distal portion 424 proximate the distal end 422. A connector 428, such as a luer connector, is assembled to at the proximal end 420. In some embodiments, the distal portion 424 defines a natural bend and is substantially flexible, such that the distal portion 424 is bendable into a substantially straight or less bent configuration upon exertion of an outside force, but will recover the natural bend upon removal of the external force (it being understood that in the view of FIG. 11, the distal portion 424 is deflected to, or held in, a straightened state).

The outer tube 412 is elongate and hollow, and defines a proximal end 430, a distal end 432, and a distal portion 434 proximate the distal end 432. In some embodiments, the distal portion 434 defines a bend and is substantially less flexible, or relatively rigid, in comparison to the distal portion 424 of the inner tube 410.

Figure 12:
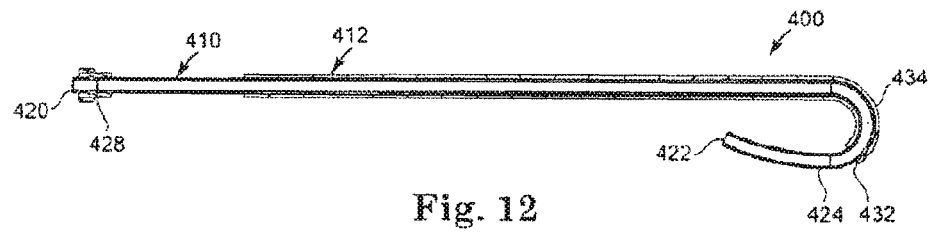
FIG. 12 illustrates the duct assembly of FIG. 11 in a deployed state.

FIG. 12 shows the duct assembly 400 of FIG. 11 in a deployed state, versus a retracted state as shown in FIG. 11. In particular, the inner tube 410 is coaxially and slidably received in the outer tube 412 such that the distal end 422 of the inner tube 410 can initially be housed within the outer tube 412 in the retracted state and be slid out of the distal end 432 of the outer tube 412 to define the deployed state. In some embodiments, the natural bend of the distal portion 424, in combination with the bend of the distal portion 434, causes the distal end 422 of the inner tube 410 to travel through an arcuate path as the distal end 422 is deployed from the outer tube 412. In operation, this allows the distal end 422 to be deployed to a target site in relatively tight areas, such as the sinus cavities. In particular, the duct assembly 400 defines a relatively elongate and compact retracted state, but can be used to curve around into hard to reach areas in the deployed state.

In terms of use, the duct assembly 400 is optionally used to functionally and/or physically replace use of the aspiration duct 132 (FIG. 8), wherein the duct assembly 400 is connected to the vacuum source 32 (FIG. 1) using the connector 428 to aspirate proximate the target site 316, for example. It should also be noted that a reinforcement member, such as one similar to the reinforcement member 192 (FIG. 8), is optionally used in association with the duct assembly 400, for example proximate the distal end 422 of the inner tube 410. Additionally, if desired, the duct assembly 400 can similarly serve instead as an irrigation duct, with a nozzle similar to the nozzle 212 (FIG. 8), for example, secured proximate the distal end 422 of the inner tube 410. Thus, where the duct assembly 400 is used, methods of biofilm removal include disposing an inlet end of an aspiration duct non-concurrently with disposing a nozzle of an irrigation duct proximate a target site, according to some embodiments where an irrigation duct and aspiration duct of the system 20 are not physically associated with one another, for example where the duct assembly 400 is used to replace (physically or functionally) features of the sheath 44 (FIG. 1), according to some embodiments.

Figure 13:
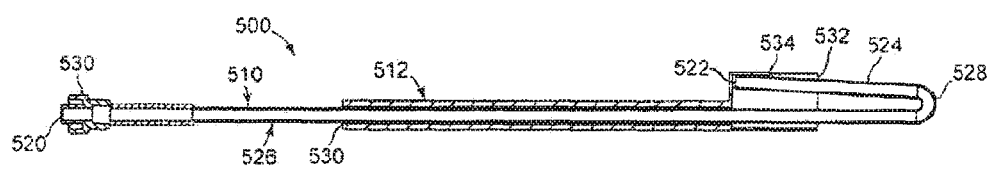
FIG. 13 is a side, cross-sectional view of another duct assembly useful with the system of FIG. 1 in other embodiments.

FIG. 13 shows an alternative duct assembly 500 optionally forming a part of the system 20 (FIG. 1). In some embodiments, the duct assembly 500 is not otherwise associated with the sheath 44 (FIG. 1) and is usable as a separate, distinct component. The duct assembly 500 includes an inner tube (or "inner cannula") 510 and an outer tube (or "outer cannula") 512.

The inner tube 510 is elongate and hollow and defines a proximal end 520, a distal end 522, a distal portion 524 proximate the distal end 522, a proximal portion 526 more proximate the proximal end 520 and an intermediate portion 528 between the distal and proximal portions 524, 526. A connector 530, such as a luer connector, is mounted to the inner tube 510 at the proximal end 520. In some embodiments, each of the distal and proximal portions 524, 526 are substantially inflexible, while the intermediate portion 528 defines a natural bend and is substantially flexible, such that the distal portion 524 is collapsible toward the proximal portion 526 into a more bent configuration upon exertion of an outside force, but will recover the natural bend upon removing the external force.

The outer tube 512 is elongate and hollow, and defines a proximal end 530, a distal end 532, and a retainer 534 proximate the distal end 532. In some embodiments, the retainer 534 is sized and shaped to receive the distal portion 524 of the inner tube 510.

Figure 14:
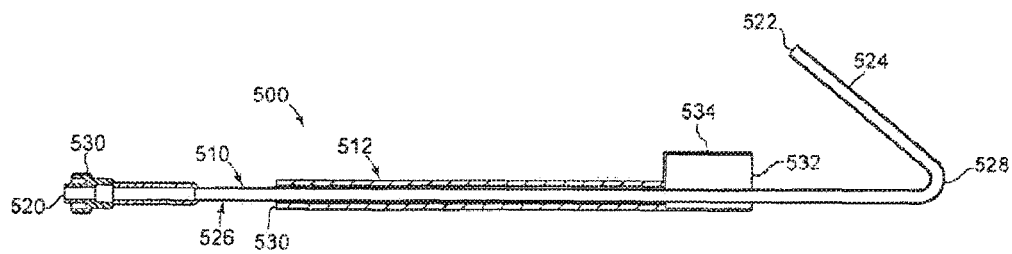
FIG. 14 illustrates the duct assembly of FIG. 13 in a deployed state.

FIG. 14 shows the duct assembly 500 of FIG. 13 in a deployed state versus a collapsed state as shown in FIG. 13. In particular, the duct assembly 500 defines a collapsed state where the inner tube 510 is coaxially and slidably received in the outer tube 512 such that the distal end 522 of the inner tube 510 is bent back toward the proximal portion 526, with the distal end 522 received in the retainer 534. The inner tube 510 is then slid distally in the outer tube 512 to release the distal end 522 from the retainer 534, such that the intermediate portion 528 transitions back to the natural bend and the duct assembly 500 defines the deployed state. In operation, inserting the duct assembly 500 in the collapsed state allows the duct assembly 500 to be deployed to a target site in relatively tight areas, such as the sinus cavities. In particular, the duct assembly 500 defines a relatively compact collapsed state, but can be used to hook or curve around into hard to reach areas, such as sinus cavities, in the deployed state.

In terms of use, the duct assembly 500 is optionally used to functionally and/or physically replace use of the aspiration duct 132 (FIG. 8), wherein the duct assembly 500 is connected to the vacuum source 32 (FIG. 1) using the connector 530 to aspirate proximate the target site 316 (FIG. 10), for example. It should also be noted that a reinforcement member, such as one similar to the reinforcement member 192 (FIG. 8), is optionally used in association with the duct assembly 500, for example proximate the distal end 522 of the inner tube 510. Additionally, if desired, the duct assembly 500 can similarly serve instead as an irrigation duct, with a nozzle similar to the nozzle 212 (FIG. 8), for example, secured proximate the distal end 522 of the inner tube 510. Thus, where the duct assembly 500 is used, methods of biofilm removal include disposing an inlet end of an aspiration duct non-concurrently with disposing a nozzle of an irrigation duct proximate a target site, where the irrigation duct and aspiration duct are not physically associated with one another. In other words, where the duct assembly 500 is used for aspiration or irrigation and is separate from the sheath 44 (FIG. 1), for example, the duct assembly 500 is disposed at the target site 316 at a different time than the sheath 44, according to some embodiments.

The systems and methods of the present disclosure provide a marked improvement over previous techniques and devices used to treat various ailments, such as chronic rhinosinusitis. By effectuating biofilm eradication using a focused, pressurized fluid, a more complete treatment is provided to the patient on a minimally invasive basis. Further, with sinus and other applications, drainage pathway(s) are restored, ventilation of the treatment site is provided (thus minimizing opportunities for biofilm re-growth), and other functional endoscopic sinus surgery treatments can be provided (e.g., topical application of medicaments, irrigation, etc.).

Although the present invention has been described with reference to preferred embodiments, workers skilled in the art will recognize that changes can be made in form and detail without departing from the spirit and scope of the present invention. For example, the duct assemblies described herein are optional components for the biofilm removal system, and thus can be eliminated, as can one or more of the other components apart from the surgical instrument.

The invention claimed is:

1. A method of removing bacterial biofilm from a target site of a human patient, wherein the method comprises:
providing a handle comprising a support portion, a gripping portion that extends from the support portion, a first irrigation duct, a first aspiration duct and a first sheath interface and wherein the first sheath interface is at a distal end of the handle and includes a first irrigation duct outlet attached to the first irrigation duct and a first aspiration duct inlet attached to the first aspiration duct;
attaching an endoscope to the support portion, wherein the endoscope comprises a working end;
covering at least a portion of the endoscope working end with a removable endoscope sheath, wherein the removable endoscope sheath comprises a second irrigation duct, a second aspiration duct and a release member, wherein the second irrigation duct comprises an outlet, wherein the second aspiration duct comprises an inlet and, wherein the removable endoscope sheath comprises a second sheath interface and wherein the second sheath interface is at a proximal end of the removable endoscope sheath and comprises a second irrigation duct inlet attached to the second irrigation duct, a second aspiration duct outlet attached to the second aspiration duct and the release member;
engaging the endoscope with the release member to retain the removable endoscope sheath on the portion of the endoscope working end;
sealing the first irrigation duct outlet to the second irrigation duct inlet with the first sheath interface and the second sheath interface;
sealing the first aspiration duct inlet to the second aspiration duct outlet with the first sheath interface and the second sheath interface;
disposing the endoscope working end, the second irrigation duct outlet and the second aspiration duct inlet proximate a target site including a layer of bacterial biofilm;
imaging the target site with the endoscope working end;
dispensing fluid through the second irrigation duct outlet toward the target site to mechanically remove at least a portion of the layer of bacterial biofilm;
collecting the removed bacterial biofilm and the dispensed fluid with the second aspiration duct inlet;
deflecting the release member to disengage the release member from the endoscope; and
sliding the removable endoscope sheath off the portion of the endoscope working end.

2. The method of claim 1, wherein the bacterial biofilm is characterized by an adhesion force and wherein the fluid is further adapted to chemically reduce the adhesion force.

3. The method of claim 1, and further comprising applying a medicament to the target site through the second irrigation duct, wherein the medicament is adapted to inhibit re-growth of the bacterial biofilm.

4. The method of claim 1, and further comprising delivering a medicament to the target site through the second irrigation duct, wherein the medicament is selected from the group consisting of a surfactant, a gel, an antimicrobial, a steroid, a growth hormone or combinations thereof.

5. The method of claim 1, wherein the flow of fluid is directed through the second irrigation duct outlet at a flow rate of between about 2 ml/s and about 12 ml/s.

6. The method of claim 1, wherein the second irrigation duct outlet and the second aspiration duct inlet are non-concurrently disposed proximate the target site.

7. The method of claim 1, wherein the target site is within a sinus cavity.

8. The method of claim 1, wherein the target site includes ciliated epithelium.

9. The method of claim 1, wherein the method is performed in treating chronic rhinosinusitis.

10. The method of claim 1, wherein the endoscope further comprises an insertion tube having a bendable distal portion and wherein the endoscope further comprises a control assembly for bending of the bendable distal portion to aim the endoscope working end in a desired direction.

11. The method of claim 10, wherein the second irrigation duct outlet is secured relative to the bendable distal portion such that the second irrigation duct outlet can be aimed with bending of the insertion tube.

12. The method of claim 10, wherein the second aspiration duct inlet is secured relative to the bendable distal portion such that the second aspiration duct inlet can be aimed with bending of the insertion tube.

13. A method of removing bacterial biofilm from a target site of a human patient, wherein the method comprises:

providing a handle comprising a support portion, a gripping portion that extends from the support portion, a first irrigation duct, a first aspiration duct and a first sheath interface and wherein the first sheath interface is at a distal end of the handle and comprises a first irrigation duct outlet attached to the first irrigation duct and a first aspiration duct inlet attached to the first aspiration duct;

attaching an endoscope to the support portion, wherein the endoscope comprises a working end;

extending at least a portion of the endoscope working end into a removable endoscope sheath, wherein the removable endoscope sheath comprises a second irrigation duct, a second aspiration duct and a release member formed therein, wherein the second irrigation duct comprises an outlet, wherein the second aspiration duct comprises an inlet and wherein the second sheath interface is at a proximal end of the removable endoscope sheath and comprises a second irrigation duct inlet attached to the second irrigation duct, a second aspiration duct outlet attached to the second aspiration duct and the release member;

engaging the endoscope with the release member on the removable endoscope sheath to retain the removable endoscope sheath on the portion of the endoscope working end;

sealing the first irrigation duct outlet to the second irrigation duct inlet with the first sheath interface and the second sheath interface;

sealing the first aspiration duct inlet and the second aspiration duct outlet with the first sheath interface and the second sheath interface;

disposing the endoscope working end, the second irrigation duct outlet and the second aspiration duct inlet proximate a target site including a layer of bacterial biofilm;

imaging the target site with the endoscope working end;

dispensing fluid through the second irrigation duct outlet toward the target site to mechanically remove at least a portion of the layer of bacterial biofilm;

collecting the removed bacterial biofilm and the dispensed fluid with the second aspiration duct inlet;

deflecting the release member to disengage the release member from the endoscope; and sliding the removable endoscope sheath off the portion of the endoscope working end.

14. The method of claim 13, wherein the bacterial biofilm is characterized by an adhesion force and wherein the fluid is further adapted to chemically reduce the adhesion force.

15. The method of claim 13, and further comprising applying a medicament to the target site through the second irrigation duct, wherein the medicament is adapted to inhibit re-growth of the bacterial biofilm.

16. The method of claim 13, and further comprising delivering a medicament to the target site through the second irrigation duct, wherein the medicament is selected from the group consisting of a surfactant, a gel, an antimicrobial, a steroid, a growth hormone or combinations thereof.

17. The method of claim 13, wherein the second irrigation duct outlet and the second aspiration duct inlet are non-concurrently disposed proximate the target site.

18. The method of claim 13, wherein the target site includes ciliated epithelium.

19. The method of claim 13, wherein the endoscope further comprises an insertion tube having a bendable distal portion and wherein the endoscope further comprises a control assembly for bending of the bendable distal portion to aim the endoscope working end in a desired direction.

20. The method of claim 19, wherein the second irrigation duct outlet is secured relative to the bendable distal portion such that the second irrigation duct outlet can be aimed with bending of the insertion tube.

21. The method of claim 19, wherein the second aspiration duct inlet is secured relative to the bendable distal portion such that the second aspiration duct inlet can be aimed with bending of the insertion tube.

* * * * *